United States Patent [19]

Murray et al.

[11] 4,061,898

[45] Dec. 6, 1977

[54] HEAT CAP

[75] Inventors: John S. Murray, Granada Hills; Sime Sunjara, Long Beach, both of Calif.

[73] Assignee: Redken Laboratories, Inc., Canoga Park, Calif.

[21] Appl. No.: 714,851

[22] Filed: Aug. 16, 1976

[51] Int. Cl.² .............................................. H05B 1/00
[52] U.S. Cl. .................................. 219/211; 128/380; 219/527; 219/549
[58] Field of Search .................... 219/211, 527-529, 219/543, 549; 128/380

[56] References Cited

U.S. PATENT DOCUMENTS

| 2,718,584 | 9/1955 | Hariv | 219/527 X |
| 3,621,191 | 11/1971 | Cornwell | 219/211 |
| 3,644,705 | 2/1972 | Johnson | 219/527 X |
| 3,869,596 | 3/1975 | Howie | 219/543 X |
| 3,988,568 | 10/1976 | Mantell | 219/527 X |

Primary Examiner—C. L. Albritton
Attorney, Agent, or Firm—Christie, Parker & Hale

[57] ABSTRACT

A heat cap for reducing processing time of permanent waves for the hair includes a cap which fits over the head, and a thermostatically controlled electrical heating element inside the cap for applying a selected heat distribution pattern to thermally-activated permanent wave solutions applied to the hair. The heating element comprises an electrical resistance heating film, preferably a meander pattern of conductive metal foil supported by a flexible, high temperature-resistant, fibrous dielectric sheet, such as aramid paper. The conductor develops a selected heat distribution pattern to be developed within the cap which, in turn, produces a generally uniform rate of heat processing for the permanent wave. The cap opens and closes along a pair of splits in the temple regions of the cap. Fasteners, preferably cooperating sections of Velcro material, are located along opposite sides of each split and are used to releasably close selected overlapping portions of the cap adjacent each split so the cap will closely conform to the size and shape of the head and the permanent wave structure to apply heat uniformly to all rollers in the permanent wave.

43 Claims, 5 Drawing Figures

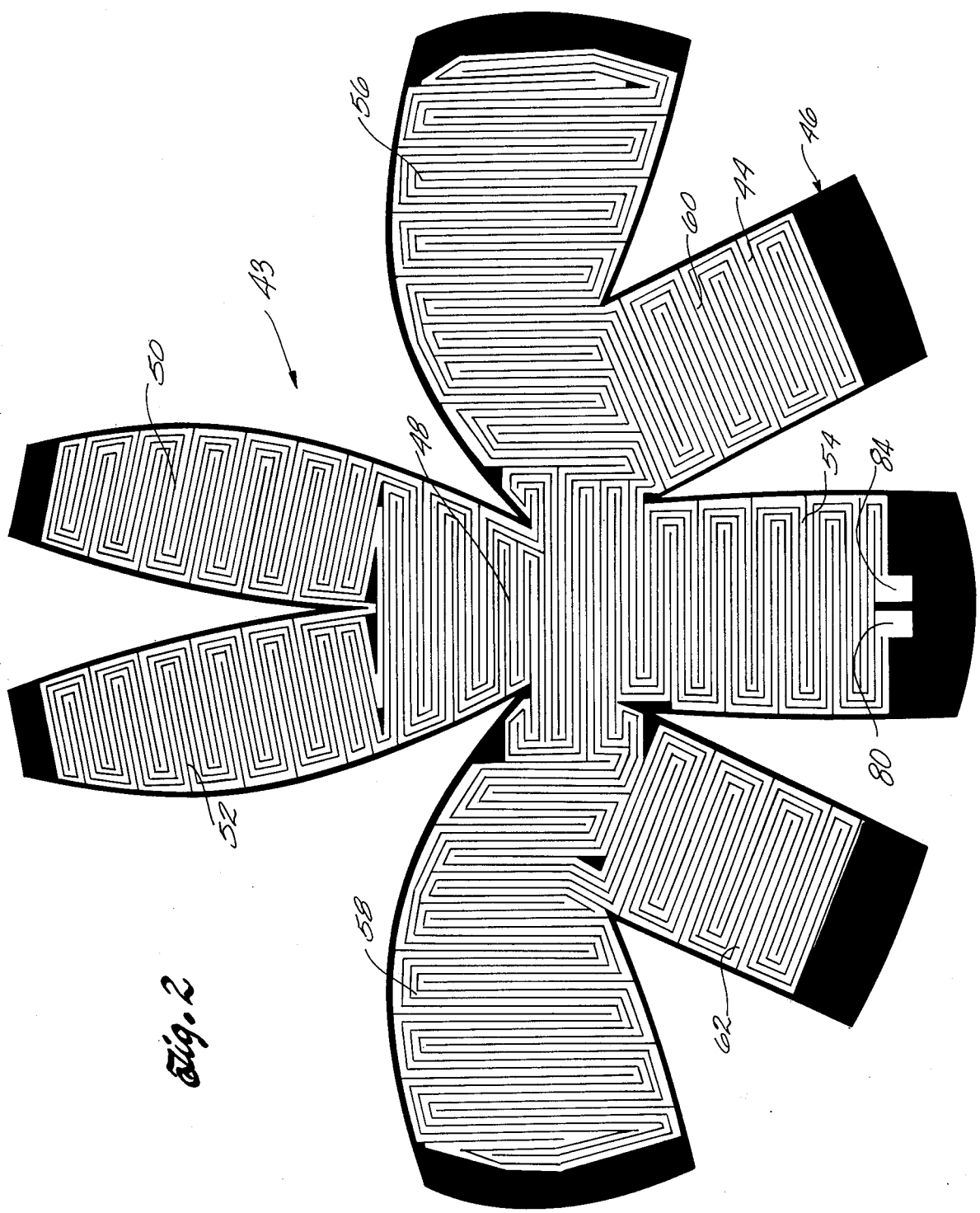

HEAT CAP

BACKGROUND

This invention relates to devices for applying heat to the hair to activate permanent wave solutions, hair reconditioners, hair bleachers, or other heat-activated or heat-accelerated solutions used on the hair.

In a process currently used by beauty shops to form permanent waves, a liqiud permanent wave solution is applied to the hair, and the hair is then coiled around a number of rollers placed about the patron's head. Commonly used low-pH permanent wave solutions contain thio-sulphur compounds, or the like, which require heat to activate the permanent wave process. In the most frequently used method of applying heat to the hair, a shower cap is placed over the head, and the patron then sits under a hot air blower which heats the permanent wave solution. During this process of applying heat to the permanent wave, the beautician must frequently remove the shower cap to check the rollers to determine whether processing is complete for each roller. Although this checking is an essential activity, it can be a tedious and time-consuming job because of the failure of the heat source to provide a uniform rate of heat processing over the entire hair structure. The inability to produce a uniform rate of heat processing also requires substantially more processing time.

To reduce the amount of time required to process permanent wave solutions, several alternatives to hot air blowers have been proposed. In one instance, it has been proposed to place an array of infra-red heat lamps around the patron's head. It has also been proposed to use an electrically heated cap which is draped over the patron's head and fits rather loosely around the head. One such heat cap includes a drawstring which ties under the patron's chin. The infra-red lamps and heat caps proposed thus far have not significantly reduced processing time. They also have other disadvantages which make them even less attractive than hot air blowers. For example, a heat lamp array can be very cumbersome to use, and known heat caps have not been developed so they can be easily removed without disturbing the permanent wave when the beautician checks the rollers in the patron's hair.

SUMMARY OF THE INVENTION

The present invention provides a heat cap which overcomes the disadvantages of the processing techniques discussed above and, in turn, produces an essentially uniform rate of heat processing for the hair.

Briefly, the heat cap of this invention, according to a presently preferred embodiment, includes a heat-resistant flexible cap structure having a hollow interior containing a flexible, sheet-like heating element for directing heat outwardly from the cap in an essentially uniform heat pattern. The cap and heating element closely conform to the three-dimensional size and shape of the permanent wave structure to effectively transfer the heat from the cap to the hair.

In a preferred form of the invention, the heating element includes an electrical resistance heating film disposed within a selected pattern throughout the interior of the cap. The heating film preferably is supported within the cap by a dielectric sheet comprising an electrically insulative material having sufficient flexibility to closely conform to the three-dimensional contour of the patron's head. The dielectric sheet is resistant to prolonged heat in the range of temperatures used with thermally-activated processing solutions for the hair.

In a preferred form of the invention, the cap opens and closes along a pair of splits extending inwardly from a lower peripheral edge of the cap. The splits provide a pair of flexible and independently movable flaps on opposite sides of the cap. Cooperating fastening means are disposed along each split for releasably attaching selected portions of the flaps to the cap in the vicinity of each split. In this way, the cap is pliable and can be quickly and easily form-fitted to the head so that the heat generated within the cap can be applied directly to all rollers used in the permanent wave with minimum heat transfer losses. This results in reduced processing time and produces a uniform rate of processing, independently of the character of the permanent wave, or the size of the rollers, for example.

Preferably, the heat element is arranged in a pattern throughout the cap which produces a selected heat distribution pattern over the area of the cap. By conforming the cap closely to the shape of the head, the selected heat distribution pattern can produce an essentially uniform rate of processing for the entire permanent wave.

These and other aspects of the invention will be more fully understood by referring to the following detailed description and the accompanying drawings.

DRAWINGS

FIG. 2 is a plan view showing an electrical resistance heating element used inside the heat cap shown in FIG. 1;

DETAILED DESCRIPTION

Figure 1:
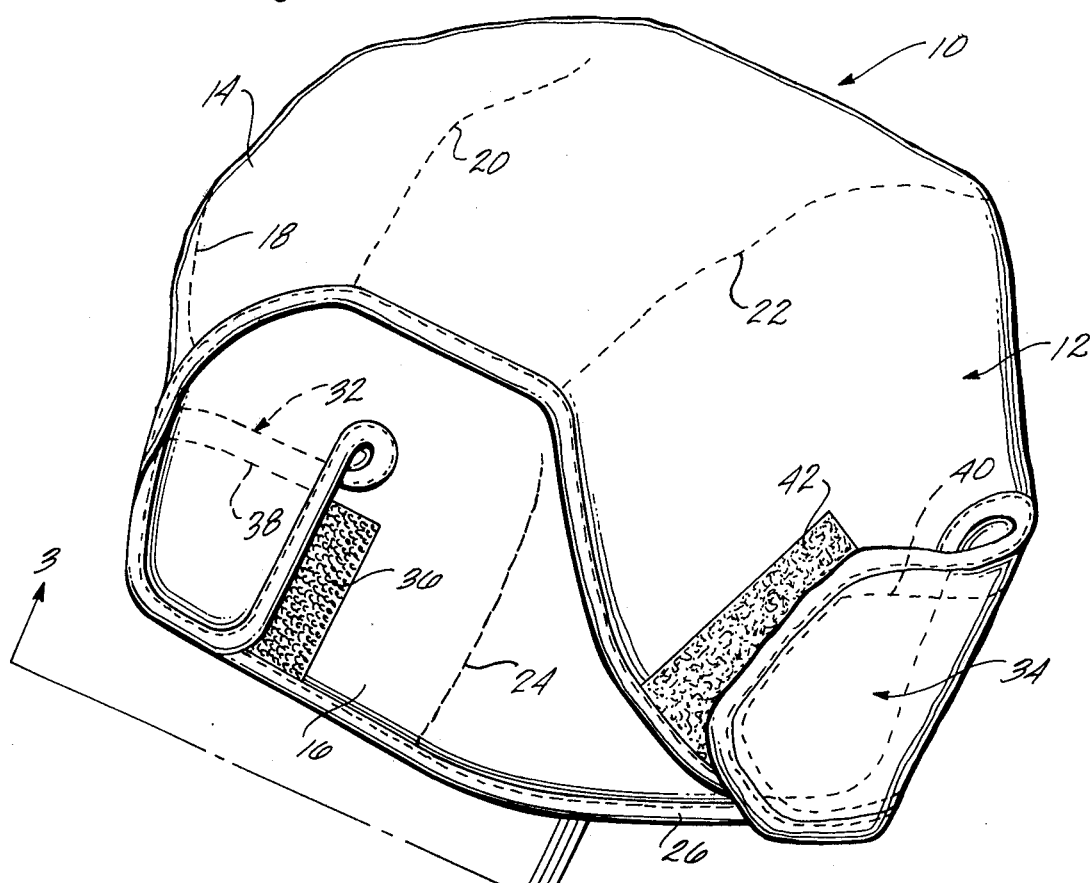
FIG. 1 is a fragmentary perspective view showing a heat cap according to this invention.

Referring to the drawings, an electrically operated hair processing heat cap 10 includes a flexible cap structure 12 for fitting over the head of a human being. The cap structure is shaped so that, in its closed position it will be generally spherically shaped to cover at least the area of the head within the hairline and to conform closely to the three-dimensional contour of the permanent wave structure for the hair.

Preferably, the cap structure 12 includes an imperforate outer cover 14 made from a heat-resistant flexible sheet-like material having good thermal insulation properties. A presently preferred material is a vinyl-coated fabric, although vinyl plastic sheeting, such as flexible polyvinyl chloride sheeting resembling leather or the like, also can be used.

The underside of the cap structure 12 includes an imperforate inner liner 16 made from a heat-resistant, moisture impermeable flexible sheet-like material. The inner liner 16 also is chemically resistant to permanent wave solutions, neutralizers, and the like which are typically used on the hair. For example, the material is resistant to chemical reducing compounds containing the mercaptan group (i.e., ammonium thioglycollate, thioglycerol, thiolatic acid, glycerol ester of thioglycolic acid, etc.). The preferred liner is made of the same material as the outer cover 14, namely a vinyl-coated fabric. Preferably, the vinyl-coated surfaces of the outer cover 14 and the inner liner 16 face the exterior of the heat cap.

The outer cover 14 and inner liner 16 each are constructed from separate sections of material initially cut into desired shapes in flat form and then stitched together to form a three-dimensional cap structure. The outer cover preferably comprises a continuous piece of material gathered together by darted stitching 18, 20 and 22 at the front of the cap and by a pair of darted stitching seams (not shown) at the rear of the cap. Similarly, the inner liner 16 is gathered by substantially indentical front and rear darted stitching. A rear darted stitching seam 24 is shown in FIG. 1. The top cover 14 and inner liner 16 are stitched together by a peripheral bias seam 26 extending around the perimeter of the cap. The perimeter bias seam improves the peripheral fit of the heat cap when the cap is conformed to the shape of the permanent wave structure.

The heat cap opens and closes along an elongated first split 28 extending inwardly from the perimeter seam 24 in the vicinity of the temple on one side of the head, and a separate elongated second split 30 extending inwardly from the perimeter seam 24 in the temple region on the opposite side of the head. Preferably each split extends inwardly from the peripheral seam by a distance less than about one-half the vertical height of the cap in its closed position. When the cap is in its closed position its vertical height is between about 7 to 8 inches, and each split extends inwardly at the temple area by a distance of about 3 inches. The first split 28 forms an independently movable flexible flap 32 in one temple region of the cap, and the split 30 forms a separate independently movable flexible flap 34 in the other temple region of the cap.

The first and second splits are arranged so that the flaps 32 and 34 will project toward the front of the head when the cap is worn on the head. FIG. 1 illustrates both flaps extending toward the frontal region of the cap. The flaps can be manipulated by the beautician to overlap adjacent temple regions of the cap. In this way, the flaps can be used to adjust the closeness of the cap to the permanent wave by pulling the flaps forward to increase their overlap with respect to the adjacent temple regions of the cap outer surface. It is preferred to use the cap by having the flaps overlap the outer surface of the cap, rather than the flaps being on the inside of the cap.

Releasable fastening means are secured to the inside surface of each flap and to the adjacent temple regions of the cap outer surface overlapped by the flaps. Although various types of fastening devices may be used, the preferred fastening means comprise cooperating types of thistle-cloth material, commonly sold under the trademark Velcro. The Velcro material is preferably spread over a substantial area of each flap and the corresponding nearby temple region of the cap. This provides means for releasably attaching the flaps to the cap in a variety of selected overlapping orientations so that the cap can be adjusted to easily conform to a wide variety of shapes and sizes of permanent wave structures. As to the heat cap shown in the drawings, the fastening means comprise a first strip 36 of hook-type Velcro material secured to the inside surface of the flap 32, a cooperating strip 38 of a pile-type of Velcro material secured to the outer surface of the cap adjacent the flap 32, a strip 40 of hook-type Velcro material secured to the inside surface of the second flap 34, and a strip 42 of pile-type Velcro material secured to the cap outer surface adjacent the flap 34. Preferably, the Velcro material covers a substantial area, each strip being between about 3 to 4 inches long and about 1½ to 2½ inches in height.

An electrical heating element 43 and controls for the heating element 43 are contained in the hollow interior area of the cap between the outer cover 14 and the inner liner 16. The electrical heating element 43 directs heat automatically from the underside of the cap to heat thermally-activated permanent wave solutions or the like used on the hair. The heating element 43 preferably comprises an electrical resistance heating film 44 of electrically conductive metal applied in a relatively thin layer to a flexible carrier sheet 46 of electrically insulative material which is sufficiently flexible to conform to the shape of the head. The electrically insulative sheet 46 (hereafter referred to as a dielectric sheet 46), also is sufficiently heat-resistant to withstand prolonged use in contact with the electrically heated film 44 at temperatures normally used in hair processing, say between about 130° to about 195° F. By way of example, certain highly flexible films made from certain synthetic resinous materials are unsuitable as a dielectric sheet for the purposes of this invention if prolonged use of the film at the high temperatures contemplated herein results in a loss of the flexible properties of the film. It has been discovered that a dielectric sheet of aramid paper provides the desired properties of long term flexibility and heat resistance. The preferred aramid paper is Nomex (trademark of DuPont) Type 410 paper which is produced from short fibers (floc) and smaller binder particles (fibrids) of a high-temperature-resistant polyamide polymer formed into a sheet product without additional binders or fillers.

Preferably, the electrical resistance heating film 44 is sandwiched between a pair of dielectric sheets 46. In the preferred form of the invention, the dielectric sheet 46 of aramid paper nearest the outside of the heat cap is 2 mil. thick and the dielectric sheet 46 of aramid paper nearest the underside of the heat cap is 3 mil. thick.

The electrical resistance heating film 44 preferably is a thin layer of chemically milled metal foil laminated between the two dielectric sheets 46. The dielectric sheets are cut into the configuration illustrated in FIG. 2 and the conductive foil is laminated between the sheets. Preferably, the foil is in the pattern illustrated in FIG. 2. The preferred configuration of the dielectric sheets enables them to cover substantially the entire surface area of the interior of the heat cap when the heat cap is in its closed position worn on the head; and the conductive foil is applied to the dielectric sheet in a pattern which covers a major area of the sheet. In this way, the heat generated, when the conductive foil 44 is energized, is spread in a substantially uniform heat pattern over the entire three-dimensional surface area heat cap. The conductive metal foil preferably is in a conductive meander pattern having substantially parallel conductive arms with narrow elongated insulating spaces between the arms and conductive bridges joining the ends of the arms. The metal foil is so thin that its thickness is minute compared with the surface dimensions of the foil, while the pattern is distributed over and occupies the greater part of the area within the boundaries of the pattern. The film is thin and flexible and provides a substantially instantaneous and relatively uniform source of heat. The heat pattern generated by the foil is uniform in the sense that heat produced in an area defined by certain dimensions of the pattern is essentially homogeneous and not subject to wide variations within the area, although the foil can be arranged to produce a heat gradient from region to region of the cap, as described below.

FIG. 2 illustrates the preferred configuration of the heating element in which the dielectric sheets 46 are cut into a pattern which provides a central region 48 for covering the top crown area of the head, regions 50 and 52 for covering left and right portions, respectively, of the front crown area of the head, a region 54 for covering the nape, regions 56 and 58 for covering left and right front portions of the crown and temple, respectively, and regions 60 and 62 for covering left and right rear portions of the crown and temple, respectively. The conductive foil 44 is preferably arranged in a pattern which will maintain the same temperature level in different areas of the head, although the heat density transferred to different regions of the head varies. To accomplish this, the foil conductor is arranged in a selected pattern to provide power densities which vary with respect to their location in the heat cap. In a preferred form of the invention, the pattern of the foil conductor 44 provides a watt density of 0.578 watts/sq.in. for the front crown, 0.525 watts/sq.in. for the top crown, 0.566 watts/sq.in. for the nape, and 0.392 watts/sq.in. for the left and right temple regions of the head. The total maximum power of the heat cap is 100 watts at 120 volts. This gradient in watt densities provides a substantially uniform rate of processing for the hair, since different areas of the hair require different amounts of heat for processing purposes. That is, the hair in the temple area of the head requires less heat density than the hair at the top of the head, and therefore the heat cap will produce a substantially uniform rate of processing.

Figure 4:
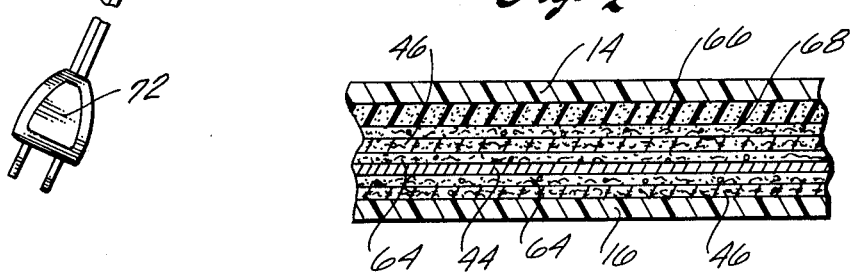
FIG. 4 is a schematic cross-sectional view, highly exaggerated in relative size, taken on line 4—4 of FIG. 3.
Figure 3:
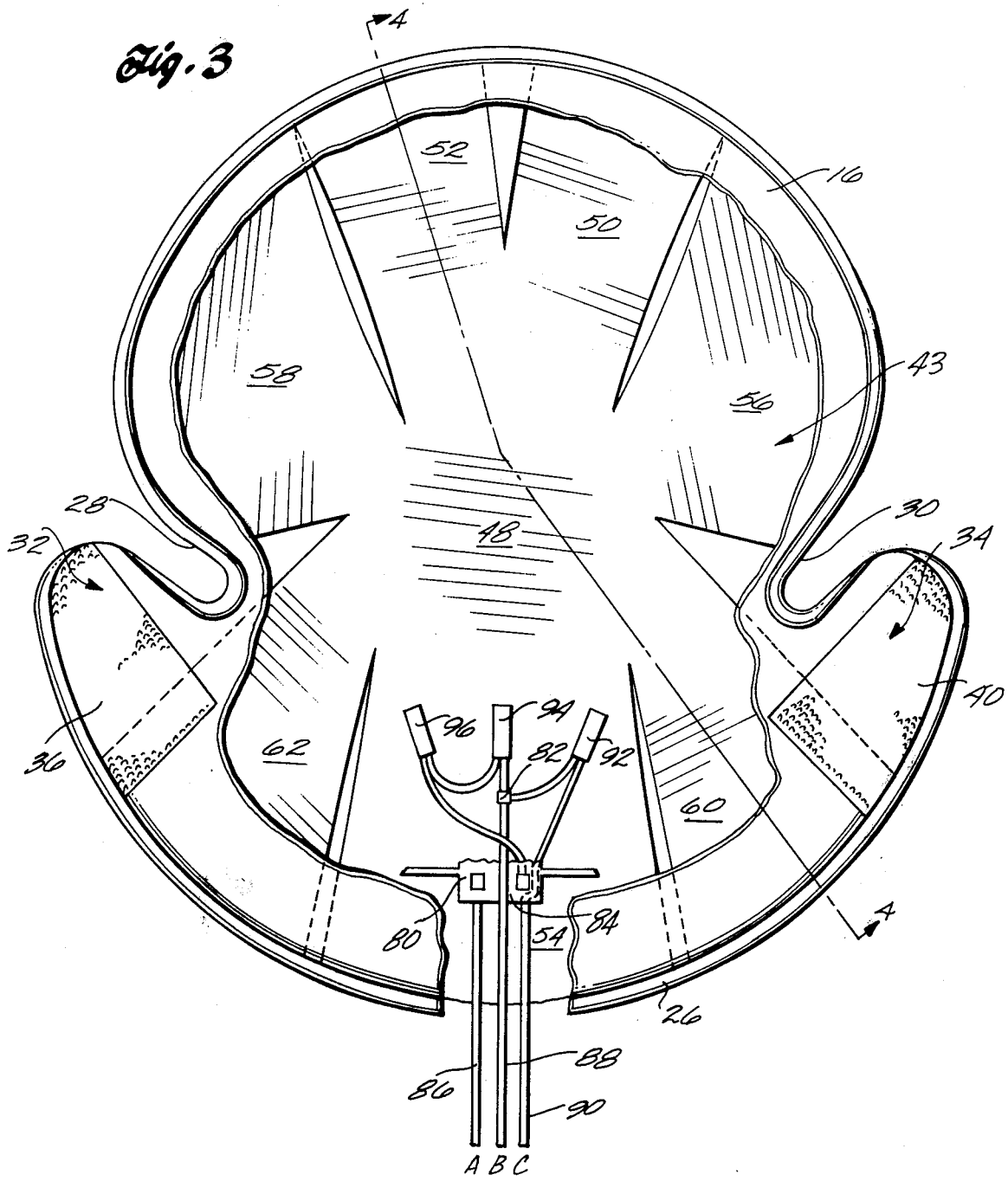
FIG. 3 is a partly schematic elevation view, partly broken away, taken on line 3—3 of FIG. 1.
Figure 5:
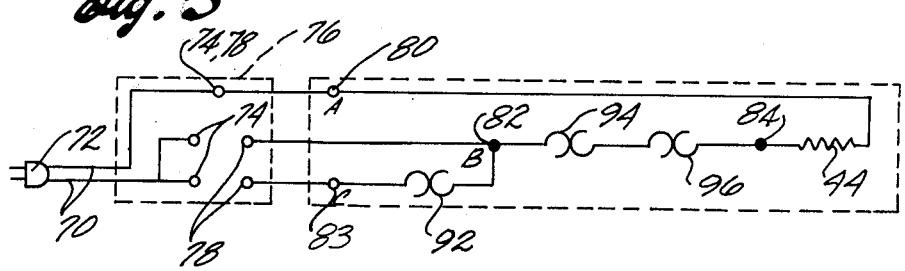
FIG. 5 is an electrical schematic diagram illustrating an electrical circuit used in conjunction with the heating element shown in FIG. 2.

FIG. 4 cross-sectionally illustrates the preferred laminated structure of the heating cap 43. The conductive foil 44 is bonded between the dielectric sheets 46 by corresponding layers 64 of adhesive, preferably an adhesive designated EC 2290 and sold by 3M Co. The conductive foil 44 is a one mil. thick foil comprising an alloy of nickel and chromium and sold under the trademark Inconel by Huntington Alloy Products, Division of International Nickel Co., Inc. Preferably, the heating element also includes a layer 66 of heat-insulative material for reducing thermal losses. The preferred insulative layer 66 is a ¼ inch thick flexible polyurethane foam having a density of 2 lbs.cu.ft. The insulating layer is bonded to the side of the heating element adjacent the outer cover 14. Preferably, the foam insulating layer 66 is bonded by a layer 68 of adhesive designated Scotch Grip 4475 sold by 3M Co.

The electrical heating system provides controls for adjusting the heat generated by the heat cap. Preferably, the electrical system includes a two-conductor electrical cord 70 having a two-prong plug 72 at one end for connection to a conventional 120 volt a.c. power source. The conductor wires of the cord 70 are connected to the primary terminals 74 of an electrical switch 76 which can be set at a low, high, or off position. The heating film 44 includes terminals 80 and 84. The secondary terminals 78 of the switch 76 are connected to the terminals 80, 82, 83 of the heating element by a three-conductor electrical cord having conductors 86, 88 and 90. The secondary side of the switch is connected to the heating element through three thermostats. A low temperature thermostat 92 has a low temperature setting, preferably 140° F. Two other thermostats 94 and 96 are connected in series and have a high temperature setting, preferably 185° F. The switch 76 applies the primary voltage between the terminals 80 and 83 in the low setting of the switch. In this setting all three thermostats are connected in series with the heating element so that the low temperature thermostat 92 controls the temperature output of the heating element. In this position the two high temperature thermostats 94 and 96 act as safety thermostats. In the high temperature setting of the switch 76, the primary voltage is applied between the terminals 80 and 82 so that only the two high temperature thermostats are connected in series with the heating element. Preferably, the thermostats are placed in a location within the interior of the heat cap overlying the portion of the heating element in the nap area of the cap. The thermostats sense the temperature at the surface of the heating element and operate so as to maintain the heating element at the temperature selected by the setting of the switch.

The present invention provides a heat cap which produces the uniform rate of heat processing especially desirable for acid-balanced, heat-activated permanent waving solutions. The heat cap also is easy to use and safe in operation. The structure of the cap makes it possible to easily adjust to various head sizes, the cap being fitted so close to the rollers that heat retention is high and processing time is substantially reduced. The cap also can be quickly and easily opened for frequent inspection of the rollers without disrupting the permanent wave structure. The use of the flexible dielectric sheet and resistive metal foil heating element provides significant advantages over a heat cap which would use electrically insulated conductor wires spaced part throughout the cap. For example, if such conductor wires were spaced apart by a distance of ½ to ¾ inch intervals, the heat differential between wires is about 40° F. Moreover, the insulation material acts as a heat sink which requires warm up time (as opposed to the present invention which does not require a warm up time) and also requires a higher operating temperature then the metal foil conductor of the present invention. In contrast, the heat cap of this invention can apply a generally uniform heat pattern to the hair, and the temperature gradient of the uniform heat pattern can vary with respect to different regions of the hair to produce a uniform rate of processing. This greatly reduces the effort required in checking the rollers and results in shorter processing time.

What is claimed is:
1. A hair processing cap for applying heat to hair on the head of a human being comprising:
flexible cap means having an outer cover, an inner liner, and a hollow interior between the outer cover and the inner liner;
the cap means having a generally spherically-shaped closed position to conform to the shape of the head and to cover the area of the head within the hairline, the cap means in said closed position having a lower peripheral edge encircling the head in the temple area thereof;
means for opening the cap comprising an elongated first split extending inwardly from the peripheral edge at one side of the cap, and an elongated second split extending inwardly from the peripheral edge at an opposite side of the cap; each split form- ing a separate flexible and independently movable flap; fastening means on each flap; and cooperating fastening means located on a portion of the cap means adjacent each respective flap, the fastening means enabling the flaps to be selectively attached to different areas of the cap in the vicinity of the first and second splits to vary the three-dimensional contour of the cap means to conform to the shape of the head; and electrical heating means in the interior of the cap means and disposed over a substantial area of the cap means for directing heat outwardly to the portion of the head covered by the cap.

2. A cap according to claim 1 in which the first split is in the vicinity of the right temple and the second split is in the vicinity of the left temple.

3. A cap according to claim 1 in which the cooperating fastening means further comprises a first type of thistle-cloth material covering each flap, and a cooperating second type of thistle-cloth material overlying said adjacent portion of the cap means so that the flaps can be selectively attached at different areas of the fastening means along each split.

4. A cap according to claim 1 in which each split traverses a distance substantially less than the height of the cap means in its closed position, said height being defined by the distance from the top of the cap means to the peripheral edge of the cap means.

5. A cap according to claim 4 in which each split extends inwardly by a distance less than about half the height of the cap means.

6. A cap according to claim 1 in which each flap has an inside face and the said adjacent portion of the cap means has an outside face, and in which the cooperating fastening means are attached to the inside face of the flap and the outside face of the cap means.

7. A cap according to claim 1 in which the heating means comprises a flexible sheet-like dielectric material, and a thin sheet-like conductive material overlying the dielectric sheet, and means for applying electrical energy to the conductive material to generate heat directed outwardly from the conductive material.

8. A cap according to claim 7 in which the dielectric material comprises a layer covering a substantial area between the outer cover and the inner liner.

9. A cap according to claim 8 in which the conductive material comprises an electric circuit formed from an electrical resistance heating film overlying the dielectric sheet.

10. A cap according to claim 9 in which the heatng film is a metal foil distributed in a meandering pattern covering a substantial area between the outer cover and the inner liner.

11. A cap according to claim 10 in which the dielectric is a sheet of aramid paper.

12. A cap according to claim 10 in which the heating means comprises a pair of said dielectric sheets, and in which the heating film is sandwiched between the dielectric sheets.

13. A cap according to claim 10 including a flexible layer of a heat-resistant, heat-insulative material between the outer cover and the heating film.

14. A cap according to claim 13 in which the insulative material comprises a layer of resilient plastic foam material.

15. A cap according to claim 10 including means for adjustably selecting the temperature of the heat generated by the electrical heating means.

16. A cap according to claim 15 in which the heat selecting means includes thermostat means disposed within the interior of the cap means for sensing the temperature of heat generated by the electrical circuit means; and means responsive to the temperature sensed by the thermostat means to control the temperature of the heat generated by the electrical circuit means.

17. A cap according to claim 6 in which the heating means is distributed throughout the interior of the cap means to generate a selected heat gradient within the cap means.

18. A cap according to claim 10 in which the cap means covers the front crown, top crown, nape, left temple, and right temple areas of the head; and the conductive film is distributed throughout the interior of the cap covering each of said areas of the head.

19. A cap according to claim 18 in which the heating film is distributed throughout the interior of the cap in a selected pattern to generate a predetermined heat density in each of said areas.

20. A cap according to claim 19 in which said pattern is selected so that the heat generated in the front crown, top crown and nap areas is greater than that generated in the left and right temple areas.

21. A cap according to claim 7 in which the outer cover comprises a heat-insulative imperforate material, and the inner liner comprises an air and liquid impermeable, heat-resistant, imperforate material.

22. A cap according to claim 21 in which the dielectric is an imperforate sheet resistant to prolonged temperatures in the range of about 130° F. to 195° F. without appreciable disruption of the flexibility of the dielectric sheet.

23. A cap according to claim 19 in which said pattern is selected so that the heat density generated in the front crown area is greater than the heat density generated in the top crown and the nape areas, and the heat density generated in the nape area is greater than the top crown area, and the heat density generated in the top crown area is greater than that generated in the temple areas.

24. A cap according to claim 1 in which the electrical heating means comprises a flexible sheet of an electrically insulative, high temperature-resistant fiberous paper material, an electrically conductive heating film bonded to the flexible sheet, and means for applying electrical energy to the conductive film to generate said heat directed outwardly from the cap.

25. A cap according to claim 24 in which the fiberous paper material is sufficiently heat-resistant to withstand prolonged use at hair processing temperatures within the range of about 130° to about 195° F.

26. A cap according to claim 25 in which the flexible sheet comprises aramide paper.

27. A cap according to claim 24 including means for operating the electrically conductive heating film at a temperature of 185° F.

28. A cap according to claim 24 in which the conductive heating film is sandwiched between a pair of said flexible sheets.

29. A cap according to claim 1 in which the inner liner comprises an air-and liquid-impermeable, heat-resistant, imperforate material and the flexible sheet is disposed in the interior of the cap immediately adjacent the inner liner for essentially uninterrupted heat flow outwardly from the flexible sheet to the inner liner.

30. A cap according to claim 29 in which each flexible sheet comprises aramid paper.

31. A hair processing cap for applying heat to heat-activated permanent wave solutions applied to the hair on the head of a human being comprising:

flexible cap means shaped to cover the area of the heat within the hairline, the cap means having an outer cover, an inner liner, and an open interior between the outer cover and the inner liner; and a flexible, sheet-like heating element disposed within the interior of the cap means for conforming to the shape of the head and for directing heat outwardly from the interior of the cap means to hair covering a selected area of the head;

the heating element comprising a sheet of an electrically insulative, high temperature-resistant, fibrous paper material; an electrically conductive heating film bonded to the flexible sheet; and means for applying electrical energy to the conductive film to generate said heat directed outwardly from the cap.

32. A cap according to claim 31 in which the fibrous paper material is sufficiently heat-resistant to withstand prolonged use at hair processing temperatures within the range of about 130° F to about 195° F.

33. A cap according to claim 32 in which the flexible sheet comprises aramid paper.

34. A cap according to claim 31 including means for operating the electrically conductive heating film at a temperature of 185° F.

35. A cap according to claim 31 in which the heating film is a metal foil in a meandering pattern covering a major surface area of the flexible sheet.

36. A cap according to claim 35 in which the flexible sheet comprises aramid paper.

37. A cap according to claim 31 in which the heating element comprises a pair of said flexible sheets; and in which the heating film is sandwiched between the flexible sheets.

38. A cap according to claim 37 in which each flexible sheet comprises aramid paper.

39. A cap according to claim 31 in which the inner liner comprises an air and liquid-impermeable, heat-resistant, imperforate material; and the flexible sheet is disposed in the cap interior immediately adjacent the inner liner for essentially uninterrupted heat flow outwardly from the flexible sheet to the inner liner.

40. A cap according to claim 39 in which the flexible sheet comprises aramid paper.

41. A cap according to claim 31 in which the electrical heating film is distributed throughout the interior of the cap to cover the front crown, top crown, nape, and temple areas of the head; and the heating film is distributed in such a pattern to generate a greater heat density in the front crown that in the top crown and nape areas, and to generate a greater heat density in the nape area than the top crown area, and then to generate a greater heat density in the top crown area than the temple areas.

42. A cap according to claim 41 in which the flexible sheet comprises aramid paper.

43. A cap according to claim 41 including a pair of said flexible sheets; and in which the electrical heating film is sandwiched between the flexible sheets.

* * * * *

UNITED STATES PATENT AND TRADEMARK OFFICE
CERTIFICATE OF CORRECTION

PATENT NO. : 4,061,898
DATED : December 6, 1977
INVENTOR(S) : JOHN S. MURRAY ET AL It is certified that error appears in the above-identified patent and that said Letters Patent are hereby corrected as shown below:

| | | | |
|---|---|---|---|
| Col. 6, line 19, | "nap" should read -- nape --; | | |
| line 36, | "part" should read -- apart --. | | |
| Col. 7, line 50, | "heatng" should read -- heating -- | (Claim | 10) |
| Col. 8, line 23, | "nap" should read -- nape --; | ( " | 20) |
| line 44, | "fiberous" should read -- fibrous --; | ( " | 24) |
| line 49, | "fiberous" should read -- fibrous --; | ( " | 25) |
| line 54, | "aramide" should read -- aramid --. | ( " | 26) |
| Col. 9, line 5, | "heat" should read -- head --; | ( " | 31) |
| line 14, | "fiber-" should read -- fibr- --; | ( " | 31) |
| line 20, | "fiberous" should read -- fibrous --. | ( " | 32) |
| Col. 10, line 22, | "that" should read -- than --. | ( " | 41) |

Signed and Sealed this

Eighth Day of August 1978

[SEAL]

Attest:

RUTH C. MASON
Attesting Officer

DONALD W. BANNER
Commissioner of Patents and Trademarks